United States Patent [19]
Allton et al.

[11] Patent Number: 5,674,206
[45] Date of Patent: Oct. 7, 1997

[54] INTRAVENOUS INJECTION SITE HAVING WIPEABLE SEPTUM AND VALVE STRUCTURE

[75] Inventors: Robert A. Allton; Thomas F. Enns, both of Mississauga, Canada

[73] Assignee: Benlan Inc., Oakville, Canada

[21] Appl. No.: 684,591

[22] Filed: Jul. 19, 1996

[51] Int. Cl.[6] .................................................. A61M 5/00
[52] U.S. Cl. ...................... 604/249; 604/256; 604/905; 251/149.1
[58] Field of Search ............................. 604/30, 33, 83, 604/86, 88, 91, 246, 247, 249, 256, 283, 284, 167, 169, 905; 215/247, 355, DIG. 3, 294; 251/149, 149.7, 149.1; 137/800

[56] References Cited

U.S. PATENT DOCUMENTS

| | | | |
|---|---|---|---|
| 4,981,469 | 1/1991 | Whitehouse et al. | 604/86 |
| 5,098,405 | 3/1992 | Peterson et al. | 604/247 |
| 5,139,483 | 8/1992 | Ryan | 604/86 |
| 5,163,922 | 11/1992 | McElveen, Jr. et al. | 604/249 |
| 5,199,948 | 4/1993 | McPhee | 604/86 |
| 5,295,657 | 3/1994 | Atkinson | 251/149.1 |
| 5,300,034 | 4/1994 | Behnke et al. | 604/167 |
| 5,351,383 | 10/1994 | Behnke et al. | 29/430 |
| 5,400,500 | 3/1995 | Behnke et al. | 29/785 |
| 5,405,326 | 4/1995 | Haber et al. | 604/110 |
| 5,441,487 | 8/1995 | Vedder | 604/167 |
| 5,474,544 | 12/1995 | Lynn | 604/283 |
| 5,540,661 | 7/1996 | Tomisaka et al. | 604/265 |
| 5,573,516 | 11/1996 | Tyner | 604/249 |

OTHER PUBLICATIONS

McGaw Inc. advertising brochure for "The Clave" IV injection port, 1993.

*Primary Examiner*—Corrine M. McDermott
*Assistant Examiner*—Cris L. Rodriguez
*Attorney, Agent, or Firm*—Donald E. Hewson

[57] ABSTRACT

A medical intravenous injection site is provided having a single piece elastomeric septum and valve combination element. The septum has a slit therein, through which a blunt cannula or a male luer slip or male luer taper can be inserted. A valve element is suspended below the septum by straps extending between the septum and valve element, and formed integrally with them as a single, one-piece elastomeric septum, valve, and strap structure. When the blunt cannula is inserted through the slit in the septum, the valve portion will be displaced away from the septum portion, and away from a valve seat formed in the interior of a substantially rigid housing in which the septum and valve structure is mounted. Fluid communication, in either direction past the valve seat, may therefore be established. Because the septum is mounted across the end of the rigid housing, it is wipeable. Thus, a needleless injection site is provided, thereby permitting injection of fluids to or withdrawal of fluids from a patient, through the injection site.

19 Claims, 4 Drawing Sheets

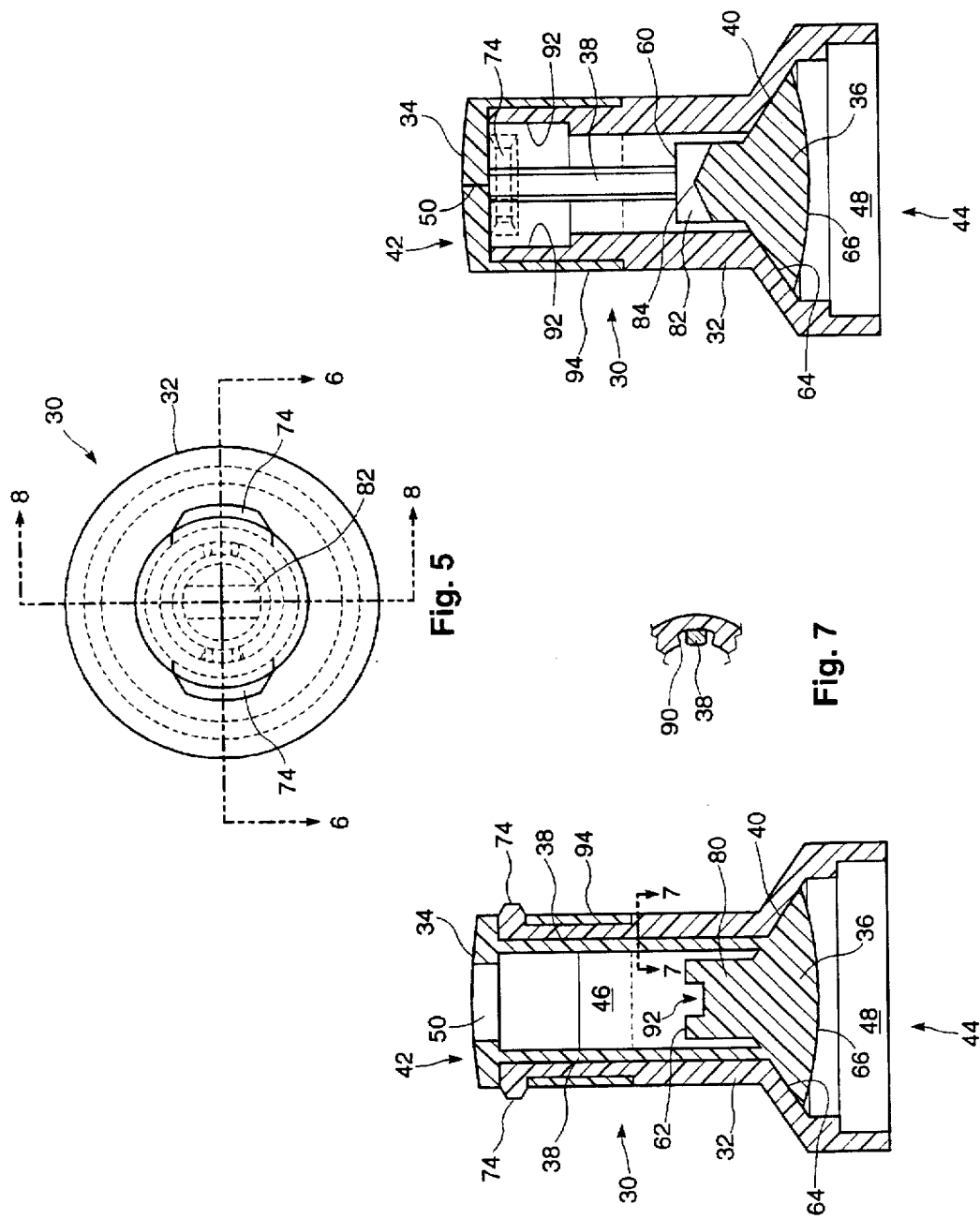

INTRAVENOUS INJECTION SITE HAVING WIPEABLE SEPTUM AND VALVE STRUCTURE

FIELD OF THE INVENTION

This invention relates to medical intravenous injection sites, and more particularly to the valves and wipeable septa used therein. Specifically, the present invention provides a medical intravenous injection site which can accommodate a standard ISO or ANSI male luer slip or male luer taper which, itself, may be passed through a slit formed in the wipeable septum of the injection site. The present invention is, therefore, applicable for use in all conditions where needleless injection sites are either desirable or required.

BACKGROUND OF THE INVENTION

Almost always, when a patient is in a hospital for either medical or surgical purposes, at some time during their stay in the hospital, the patient will be connected to an intravenous set for purposes of supplying nutrients, medicines, anaesthetics, and so on, to the patient, or for purposes such as to withdraw blood for sampling from the patient. In such conditions, an intravenous site is established on the patient, usually in the hand or forearm of the patient, and that intravenous site may remain established in the patient for a period of several days or more. In any event, the intravenous set which is then established may have several injection sites established in it, joined together by typical intravenous catheter tubing, through which fluids may be injected or withdrawn. Quite often, an injection site will take the form of a so-called "Y"-fitting, due to its general configuration, so that nutrients, medications, or anaesthetics, may be delivered to the patient, or blood or other body fluids withdrawn from the patient.

Very often, it is desirable, and quite often it may be mandated, that each injection site within the intravenous set shall be established as a needleless site. By that, it is meant that use of a sharp needle will be precluded. Obviating the necessity for use of a sharp needle in an intravenous set thereby precludes risk of accidental injury, or worse, when they are working at the injection site.

However, this raises a new problem, in that whenever an injection site is established, it must be sealed except when it is desired to inject or withdraw fluid through the injection site; and that, in turn, means that the septum which seals the injection site should be wipeable in order to preclude airborne infectious agents, germs, microbes, and the like, that may find themselves to the injection site and thence into the intravenous set when the interior of the intravenous set is accessed. By wiping the outer surface of a septum which is essentially positioned as a cap at the exterior of the injection site with a suitable antiseptic product, usually 70% isopropyl alcohol, the risk of infection from any contaminating agent passing through the injection site and intravenous set into the patient, is substantially precluded.

However, heretofore, most previously available intravenous injection sites, needleless valves and connectors, etc., have either failed to provide a structure having a wipeable septum, or they have done so either with non-standard dimensions and fitments, or with structures having high degrees of complexity and concomitant higher costs. Indeed, many needleless injection sites require the use of an external cap which, if it is removed for any period of time, or if it is forgotten to be replaced, may require replacement of the injection site with a new, sterile injection site. Further discussion of prior art devices with follow, hereafter.

When an intravenous set is in use, each injection site must, of course, be sealable, in that the septum must be of an appropriate material and/or of an appropriate design that, after a blunt cannula or male luer slip or male her taper has been inserted and removed therefrom, it will re-seal. Typical materials for those purposes are silicone rubber, or other thermoplastic elastomers, discussed hereafter. Latex may be considered.

Still further, an injection site must function as, or include as part of its structure, a valve. Moreover, that valve must be configured so as to permit two-way fluid flow past the valve, so that fluids may either be injected into or removed from a patient. Moreover, the valve must be capable of withstanding back pressure created against it in some circumstances, as discussed hereafter.

It is also important to note that an intravenous injection site which is constructed in keeping with the present invention will accommodate a blunt cannula, and in particular the more typical male luer slip or male luer taper. This feature has far reaching advantages, because hypodermic syringes and the like ordinarily require at least the further assembly of a cannula placed over the male luer slip or male luer taper formed at their end, instead of a hypodermic needle, for transfer of medications or other fluids from the syringe into the injection site for delivery into the patient. Thus, as will be described in greater detail hereafter, while the present invention is generally adapted for use with blunt cannula, it is particularly adapted for use with an ordinary male luer slip or male luer taper. This provision is one that has heretofore been made only with respect to an expensive and complicated structure.

Of course, a number of advantages come from the use of blunt cannula or, more particularly, from the use of blunt male luer tapers, including the fact that they will not pierce the skin of a health worker or other medical personnel. The safety of such personnel, and the elimination of the use of medical sharps, is therefore assured. It is noted that the terms "male luer slip" and "male luer taper" are interchangeable, and refer in fact to an identical structure. For purposes of discussion hereafter, the term "male luer taper" is employed.

Very often, but not always, it is appropriate to physically connect a device such as a hypodermic syringe to an injection site, for injection of or withdrawal of fluids to or from the patient. That physical connection is most often effected by turning a standard luer lock collar onto a threaded portion, or a pair of lugs, located at the outer and upper end of the injection site, in the same region as the septum is located. Thus, in a particular embodiment of the present invention, there is provision of means for being received in and mated to a standard ISO or ANSI luer lock collar. Accordingly, injection sites in keeping with the present invention are effectively standardized, so that any other standardized medical injection or withdrawal apparatus that is normally used with an intravenous set may be used with the injection sites of the present invention. This, in turn, may be of beneficial value to the hospital administrators who are required to purchase and maintain appropriate inventories of intravenous set hardware, as economically as possible.

DESCRIPTION OF THE PRIOR ART

Several examples of prior art patents, and one other commercially available product, are discussed below. Some of the prior art references are discussed because they provide teachings of typical prior art devices, and because they may have particular relevance or, alternatively, because they may teach structures having particular shortcomings either as to design philosophy and criteria, or as to complications of structure leading to expensive devices.

For example, U.S. Pat. No. 4,981,469, issued to WHITE-HOUSE et al, provides a septum cap which may be locked to a male luer lock connector. However, the septum is located in the interior of the septum adaptor assembly and is not wipeable. Thus, an external cap must be fitted into place at the end of an annular neck extending away from the septum.

PETERSON et al U.S. Pat. No. 5,098,405 issued Mar. 24, 1992 describes a catheter adapter having a side port connection, and which includes a combination valve whose purpose is to prevent back-flow from the patient. While the purpose is to provide a structure which will permit infusion of medications or the like through either an axial port or a side port, providing automatic shut off when the infusion pressure becomes lower than the ambient pressure within the body of the patient, several valve structures are required. The outlet of the catheter adapter is provided with a luer collar. A mating male luer connector may be connected to the axial inlet port, which may itself be connected using a luer collar; however, there is no provision for a septum, and thus there is no provision for maintaining sterility at the inlet port.

RYAN U.S. Pat. No. 5,139,483 is particularly directed to a quick connect/disconnect device for use with a typical intravenous administration system. However, the Ryan device provides a structure having a septum which may be wipeable, but which only serves to be pierced by a needle. In other words, the Ryan device does not contemplate needleless injection or withdrawal of fluids to or from a patient.

On the other hand, MACFEE U.S. Pat. No. 5,199,948 is specifically directed to a needleless valve. Here, an injection set is provided with a slit septum which has a concave end and a peripheral flange which is captured in a cap which causes the concave end to bulge and flatten, thereby improving the sealing of the slit in the septum. The other end of the housing in which the septum is placed is, in turn, configured as a tapered stem, whose purpose is to be inserted into the receptacle end of a catheter. A drug transfer spike is, however, be required to be inserted through the slit formed in the septum; and, while the drug transfer spike has a rounded end, it is nonetheless sufficiently sharp that some risk to medical personnel still exists. There is no separate valve structure or element that is provided; and thus, the septum itself may be required to withstand back pressures against it, in some circumstances.

Yet another injection site which will accept and accommodate a blunt cannula passed through a wipeable septum is taught in U.S. Pat. No. 5,300,034 to BEHNKE et al. Similar structures are also taught in related Behnke et al U.S. Pat. No. 5,351,383, and No. 5,400,500. In this case, the septum is formed with a slit, which is preferably located in a slightly recessed end, and when the blunt cannula is passed through the septum it is sealed at its periphery by the septum. No valve structure is provided.

A disposable safety syringe is taught in HABER et al U.S. Pat. No. 5,405,326 issued Apr. 11, 1995. However, this structure requires the use of a needle shuttle located within the main barrel of the syringe, adapted at its inner end with a spike which will penetrate the septum of an ampoule mounted within the barrel, and adapted at its outer end to accommodate a standard luer lock needle assembly. Thus, this safety syringe is intended only for use with a sharp needle. On the other hand, a structure which is not dissimilar to the blunt nose portion of the needle shuttle, which is intended to engage to a sharp standard needle having a luer lock assembly will, of itself, be accommodated by an injection site in keeping with the present invention.

VEDDER U.S. Pat. No. 5,441,487 provides teaching for a needleless injection site which will, indeed, accommodate a blunt cannula such as a male luer taper at the distal plastic end of a typical syringe structure. A septum or closing web is provided with a slit, through which a male taper of a male luer lock fitting may pass, so as to provide fluid communication to the interior of the medical site structure. However, within the interior of the structure there is a very complicated valve arrangement, comprising a disk valve having an actuator and a resilient disk, seated on a nipple within the housing. In order for the valve to be opened, the male luer taper is forced downwardly against the actuator which pushes against the resilient disk, causing it to deform and thus permitting flow past the region where the disk seats against a valve seat. The interior of the actuator is hollow, so as to provide a fluid flow path from the syringe through the injection site. However, the injection site is configured having the septum which is bonded only to the interior of an upper cylindrical body portion, the exterior of which is not standard but which may mate and lock to a standard ISO or ANSI male luer lock and taper. The outer exterior surface of the septum is wipeable. The only manner in which the needleless valve housing may be operated is for a male luer taper and associated male luer lock or collar to be physically connected to the injection site, in order to depress and open the complicated, two-part valve structure.

Finally, an intravenous injection port is provided for needleless administration systems using blunt cannula associated with male luer locks, supplied by McGaw, Inc. in association with the trade mark CLAVE (trade mark of ICU Medical, Inc.). Here, a septum is provided which has a tapered interior chamber facing the outlet side of the connector; and, when a luer lock is connected to the body of the injection port, the septum is compressed and fluid flow is permitted. Removing the luer lock causes the septum to return to its closed and sealed position. The exterior end of the septum is located at the end of the injection port body, so that it is wipeable. However, because there is no specific valve structure, the ability of the device to withstand back pressures is unknown.

OBJECTS OF THE INVENTION

It is a principal object of the present invention to provide an injection site for use as an intravenous injection site in needleless intravenous set systems.

A particular purpose of the invention is to provide such an intravenous injection site having a wipeable septum, and a valve structure, whereby asepsis may be assured, and wherein the valve will withstand significant back pressures against it.

Yet another purpose of the present invention is to provide an intravenous injection site having a wipeable septum and a valve, which will function bi-directionally. That is, fluids may be injected into, or withdrawn from, a patient, by employing the injection site of the present invention.

Accordingly, in at least one embodiment of the present invention, the intravenous injection site having a wipeable septum and valve structure may be configured in a "Y"-site embodiment.

Moreover, an intravenous injection site in keeping with the present invention may be functional, whether or not a male luer taper that is connected to it is held in place by a male luer lock collar. Thus, the injection site may be used momentarily, such as for periodic injection of various medications, or withdrawal of blood samples; or it may be used in a longer term arrangement such as for connection to an intravenous drip bag or the like.

Accordingly, the structure of the intravenous injection site and wipeable septum must be such that it may be accessed many times during the time when it is in place in an intravenous set connected to a patient.

SUMMARY OF THE INVENTION

Thus, in keeping with one aspect of the present invention, there is provided a medical intravenous injection site which comprises, in combination, an elastomeric septum, an elastomeric valve element, and a substantially rigid housing. The medical intravenous injection site of the present invention is adapted to receive a blunt cannula, including particularly a standard ISO or ANSI male luer slip or male luer taper. The substantially rigid housing is configured so as to have an internally disposed annular valve seat formed therein, and has a first opening at an injection end of the housing and a second opening at a patient end of the housing. A first passageway extends through the housing between the first opening and the annular valve seat, and a second passageway extends through the housing between the annular valve seat and the second end, with the first and second passageways connecting the first and second ends of the rigid housing in fluid communication one with the other, when the valve is open.

The elastomeric septum and elastomeric valve element comprise a single, one-piece elastomeric septum and valve combination element, which has a septum portion, a valve portion, and at least one strap portion extending between the septum portion and the valve portion. Usually, there is a pair of diametrically opposed straps.

The septum portion is positioned at the injection end of the rigid housing so as to cover the first opening thereof, and thereby so as to present a wipeable septum surface at the exterior of the injection end. The patient end of the rigid housing is configured as a socket, whereby it may be connected to an end of an intravenous tube or catheter, or other medical device, in any usual manner.

The septum portion has at least one elongate slit formed therein, through its thickness, and across a portion of a diameter thereof. The elastomeric septum portion is deformable so as to permit a blunt cannula to pass through the slit and into the first passageway.

The valve portion has an upper face which faces towards the septum portion, and a valve seating face which co-operates with the annular valve seat so as to form a closeable valve when the valve seating face and the annular valve seat are in contact with each other. There is a lower surface on the valve portion which is opposed to the upper face and the valve seating face.

The length of the elastomeric strap portion is such that it urges the valve seating face into contact with the annular valve seat when the strap portion is at rest and is not distended beyond its rest position. However, when the at least one strap portion is distended—that is, stretched—so that the valve portion is moved away from the annular valve seat towards the second end of the rigid housing, which will occur when a blunt cannula contacts the upper face of the valve portion and is advanced against that upper face so as to distend the strap portion, then the closeable valve is opened so as to permit fluid flow past the valve in either direction between the first passageway and the second passageway.

In general, the valve portion is configured so as to have a centrally located cylindrical neck portion extending away from the valve seating face and up to the upper face of the valve portion, and there is a channel formed in the upper face. The channel is in a direction perpendicular to a line drawn between a pair of diametrically opposed strap portions, and thus the channel with provide a fluid flow pathway.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

FIG. 5 is a plan view at the injection or upper end of an injection site;

FIG. 6 is a sectional view taken along the lines 6—6 in FIG. 5;

FIG. 7 is a partial sectional view taken along the lines 7—7 in FIG. 6; and

FIG. 8 is a sectional view taken along the lines 8—8 in FIG. 5.

DETAILED DESCRIPTION OF THE PREFERRED EMBODIMENTS

Figure 1:
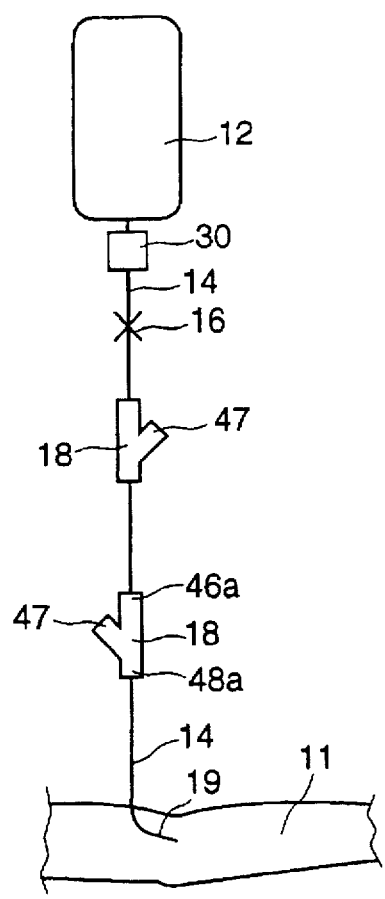
FIG. 1 is essentially a schematic illustration of a typical intravenous set in which injection sites of the present invention are employed.

A typical intravenous set 10 is shown schematically in FIG. 1. It may comprise an intravenous drip bag 12 connected by a typical catheter tubing line 14 to a portion 11 of a patient, which is otherwise undefined. The lower end of the catheter line 14 terminates in a needle 19 which is placed into a vein in the patient's body. The needle 19 is the only medical sharp which will be employed while the intravenous set is in place; all other devices that will be used for injection or withdrawal of fluids from the patient will employ blunt cannula.

Typically, a valve 16, or several valves, will be employed in the intravenous set so as to close the catheter 14, and thereby preclude flow through the catheter 14 in either direction from above or below the valve. The intravenous set 10 is shown having two injection sites 18, and an injection site 30. The injections sites 18 each are in the form of a "Y"-site; the injection site 30 may be a linear injection site having the more typical embodiment shown in FIGS. 4 through 8.

However, it must be noted that each of the "Y"-sites 18 will comprise two passageways which combine and communicate with an exit passageway, and that the elastomer septum and valve combination element, which is an important feature of the present invention, will be found in at least one of those two passageways in each "Y"-site, if not in both passageways. That matter is discussed hereafter.

Figure 2:
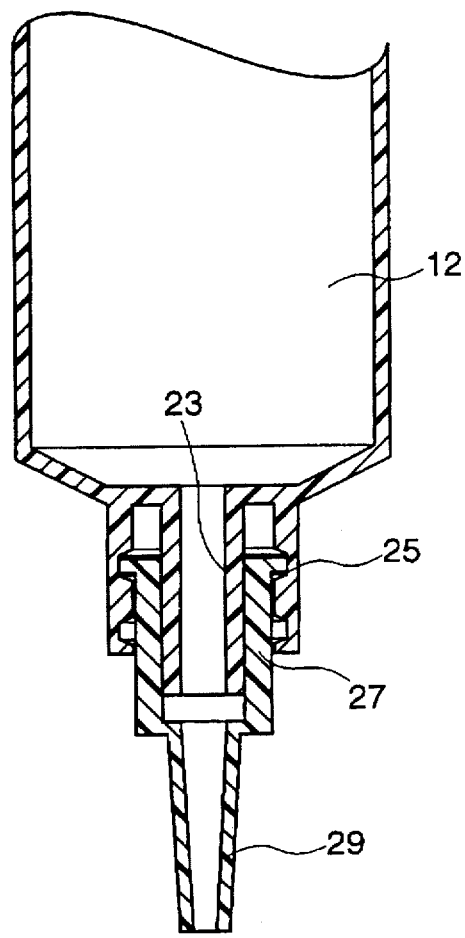
FIG. 2 is a cross-sectional view of a portion of a typical prior art hypodermic syringe using a blunt cannula for injecting or withdrawing fluid to or from a patient.

Before proceeding to a detailed discussion of the specific features of the intravenous injection sites in keeping with the present invention, a typical prior art structure, as shown in FIG. 2, will be described. Here, an end of a syringe 21 is shown, which terminates in a male luer taper 23, which is part of a standard luer lock which also comprises a luer collar 25. However, it has been the general practice that either a medical sharp or, at best, a fine but blunt cannula is fitted to the luer lock 23, 25 of the syringe 21, for purposes of injection or withdrawal of fluids to or from a patient. Thus, a standard luer injection needle may be fitted to the syringe 21; or, as shown in FIG. 2, a standard luer blunt cannula having a socket 27 and blunt cannula extension 29 may be used. Generally, the materials of the syringe, luer lock, and blunt cannula, may be suitable plastics. However, the blunt cannula or luer fitting medical sharp if used, may be metallic or combination plastic and metal. In any event, with few exceptions, it has been necessary to at least fit a blunt cannula to a syringe in order for the syringe to be used to inject or withdraw fluids to or from a patient through an intravenous injection site.

The one exception which is known is the Vedder U.S. Pat. No. 5,441,487, noted above. That patent describes an injection site having a structure including a septum and valve which will mate to and be actuated by a blunt cannula such as a male taper of a male luer lock, and having a wipeable septum. However, it is imperative that the luer lock must have a nut or collar which must be turned onto a tapered upper portion of the needleless valve housing in order for the valve to be actuated and thereby opened. Moreover, the Vedder needleless valve housing must, in turn, be connected to yet another male luer lock fluid connector in order for there to be fluid communication to a catheter. The Vedder structure, therefore, presents a complicated and expensive needleless injection site.

Quite unexpectedly, however, the present inventors have discovered that they can provide an intravenous injection site which has a wipeable septum and a valve structure which is easily operated, without the necessity in all instances for actuation of a luer lock, and which provides a valve through which two-way fluid communication can be established. These advantages are particularly reached by employing an elastomeric septum and valve combination element which is molded as a single, one-piece element. By the provision of that one-piece element, a more simplified housing structure may be provided, thereby resulting in a more economical device. It must be kept in mind that all such devices are single use devices, although they may be maintained in continuous use for a period of up to several days with the patient, after which they are disposed of. The cost of such devices is, therefore, of significant interest to hospital administrators and the like.

Turning now to FIGS. 4 through 8, details of a typical, single axis, medical intravenous injection site in keeping with the present invention are shown. As will be described hereafter, many of those details are just as equally applicable to the construction of a "Y"-site, such as either "Y"-site 18, shown in FIG. 1.

Figure 3:
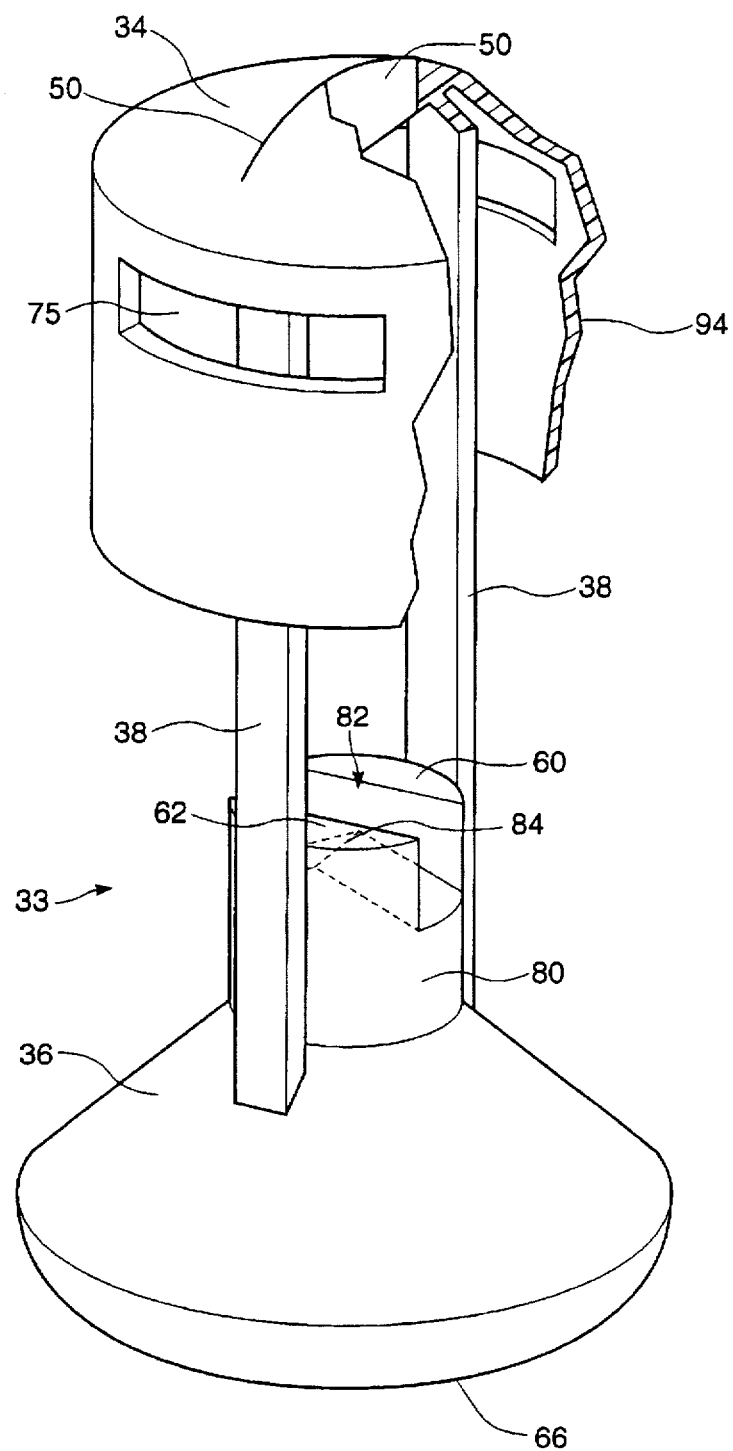
FIG. 3 is a perspective view of a single, one-piece elastomeric septum and valve combination element in keeping with the present invention.

In any event, there is shown in an appropriate manner in any of FIGS. 4 through 8 a medical intravenous injection site having a substantially rigid housing 32, an elastomeric septum 34, an elastomeric valve element 36 and, in the usual embodiment, a pair of strap portions 38. The elastomeric septum element 34, the elastomeric valve element 36, and the elastomeric strap portions 38, are molded as a single, one-piece combination element 33, which is also shown in FIG. 3.

The housing 32 is configured so as to have an internally disposed annular valve seat 40 formed therein. The housing 32 has a first opening 42 at its injection end, and a second opening 44 at the distal or patient end thereof. The injection end 42 is so-called because medications, nutrients, anesthetics, and so on, are injected into the intravenous set at that end. However, as noted, body fluids may also be drawn from the patient by an appropriately arranged syringe or receptacle which is connected at the first or injection end of the intravenous injection site housing.

Figure 4:
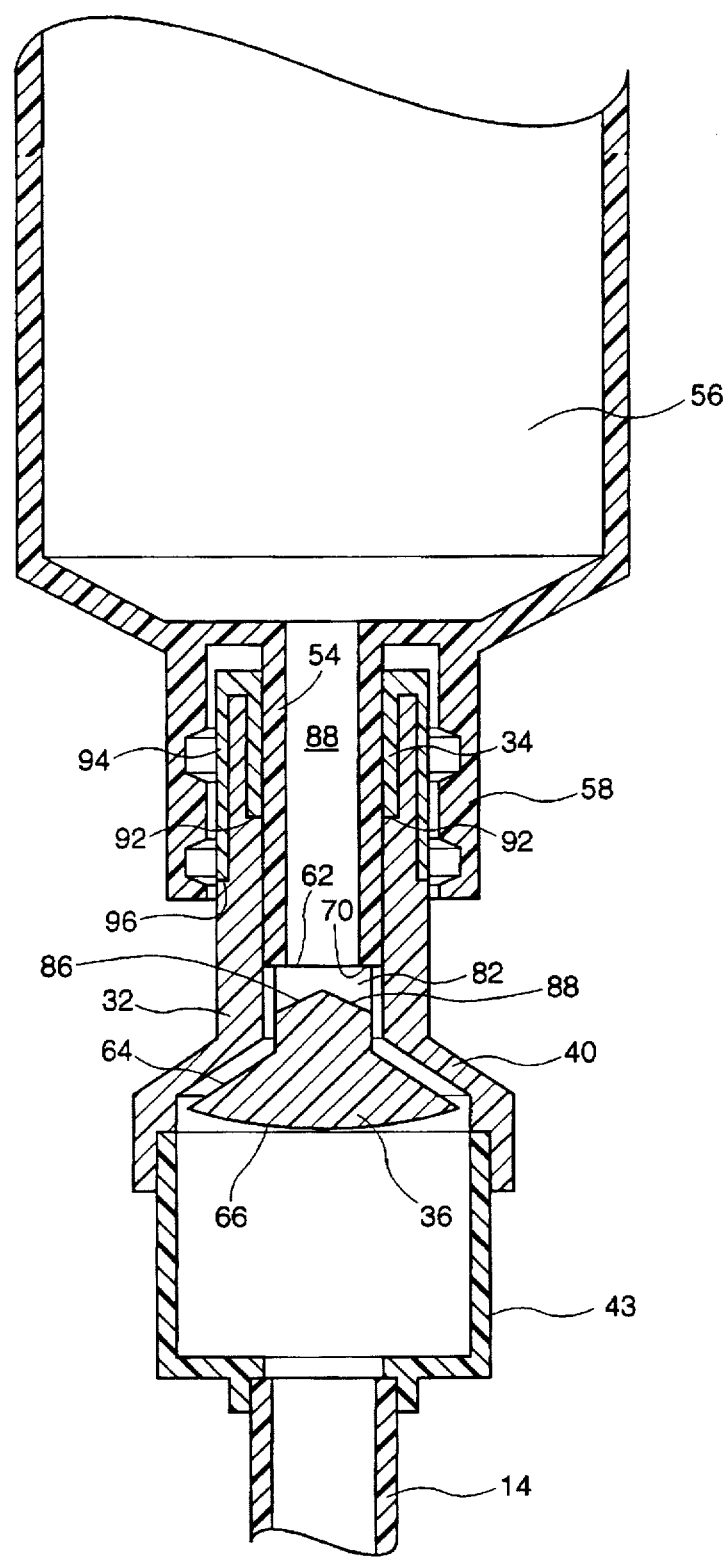
FIG. 4 is a cross-sectional view of a portion of a syringe in use together with an injection site in keeping with the present invention.

A first passageway 46 is disposed within the substantially rigid housing 32 and extends between the first opening 42 and the annular valve seat 40. A second passageway 48 extends between the annular valve seat 40 and the opening 44 at the patient or second end of the housing 32. Thus, the first and second passageways 46, 48 connect the first and second ends 42, 44 of the housing in fluid communication with one another, when the valve is open as shown in FIG. 4 and as discussed hereafter.

While the single, one-piece element 33 is generally configured so as to have two strap portions 38, it is possible that a single strap portion which extends substantially around the circumference of the combination element 33 could be provided. In that case, of course, the combination element 33 is otherwise configured so as to permit fluid flow through it, and past the valve element 36, as discussed hereafter.

As is seen particularly in FIGS. 6 and 8, the septum element 34 is positioned at the injection end 42 of the housing 32 so as to cover the first opening in the housing, and thus so as to present a wipeable septum surface at the exterior of the injection end of the injection site. The provision of a wipeable septum is, of course, important, as has been discussed above. Any contaminants which may come to rest on the outer surface of the septum 34 may be either wiped away, or at least a condition of asepsis will be established, by wiping the outer surface of the septum using an antiseptic solution such as 70% isopropyl alcohol.

The patient end 44 of the rigid housing 32 is configured as a socket, and may connect directly to an end of an intravenous tube, or through an intermediary connector. It is contemplated, therefore, that the socket end of the housing 32, at 44, may function as a female socket into which the end of a catheter tube may be inserted; or an adapter 43, as shown in FIG. 4, may be put into place for connection to the intravenous tube or catheter tubing 14.

A slit 50 is formed in the septum portion 34, through its thickness as shown in FIG. 6, and across at least a portion of the diameter of the septum portion 34 which overlies the injection end 42 of the housing 32. The septum 34 is deformable, and thus a blunt cannula will be permitted to pass through the slit 50 and into the first passageway 46, in the manner shown in FIG. 4. There, a male luer taper 54 is shown having been inserted through the slit 50 of the septum 34, and into the first passageway 46. The syringe 56 is also shown as comprising a luer collar 58, so that the male luer taper 54 and the collar 58 may comprise a luer lock.

The valve portion 36 has an upper face 60, 62, which faces towards the septum portion 34, and a valve seating face 64 which faces and co-operates with the annular valve seat 40, so as to form a closeable valve when the valve seating face 64 and the annular valve seat 40 are in contact with each other. There is also a lower surface 66 which is opposed to the upper face 60, 62 and the valve seating face 64.

As can be best seen from FIG. 6 and 8, the length of the elastomeric strap portion or portions 38 is such as to urge the valve seating face 64 into contact with the annular valve seat 40, when the strap portion or portions 38 are not distended beyond their rest position as assembled within the housing 32 of the intravenous injection site 30. In general, that means that the length of the strap portions 38 is such that it is slightly shorter than the distance between the injection end 42 and the valve seat 40 which the strap portions 38 occupy, so that the strap portion or portions are very slightly in tension. Thus, the valve seating face 64 is urged into contact with the annular valve seat 40, and thus a sealed and closeable valve structure is provided.

However, as noted, the at least single strap portion 38 is elastomeric and is distendable, so that the valve seating face 64 may be moved away from the annular valve seat 40 in a direction towards the second end 44 of the housing 32. This is accomplished by the end 70 of the blunt cannula 54 contacting the upper face 60, 62 of the valve portion 36 of the one-piece elastomeric combination element 33. When the end 70 of the blunt cannula is advanced against the upper face 60, 62, the strap portion or portions 38 are stretched and are thus distended, and the valve is opened. It is clear in FIG. 4 that fluid flow past the valve and between the valve seating surface 64 and annular valve seat 40 will be permitted in either direction between the first passageway 46 and the second passageway 48 found in the housing 32 of the injection site 30.

As noted, generally the combination element 33 is configured so as to have a pair of diametrically opposed strap portions 38, and the discussion hereafter assumes that configuration.

It has been found to be appropriate that the septum portion 34 has but a single slit 50 formed therein. It has been noted above that a male luer taper 54 may be passed through the slit 50, and it is the intent of the present invention that such a male luer taper shall be in keeping with ISO or ANSI standard dimensions. This permits a hospital administrator to purchase supplies such as syringes, connectors, and the like, from one or more manufacturers who adopt the ISO or ANSI standards. Moreover, it is important to note that, by appropriate choice of materials and by dimensioning the slit 50 so that it extends for an appropriate portion across the diameter of the septum portion, a male luer taper, rather than a prior art blunt cannula as discussed in association with FIG. 2, can be accommodated. The precise dimension of the slit 50 may be, in part, determined by which material for the elastomeric one-piece combination element is used, as discussed hereafter.

The exterior of the housing 32 may be provided, at or near the injection end 42, with such as a pair of lugs 74, as shown in each of FIGS. 5, 6, and 8. The provision of the pair of lugs thus conforms the outer surface of the injection end of the housing so as to be received in and mate to a standard ISO or ANSI luer lock collar—for example, the luer lock collar 58, shown in FIG. 4. Thus, any male luer taper 54, associated with a luer lock collar 58, will permit a more or less permanent connection of a device which terminates in a male luer taper to an injection site in keeping with the present invention. By "permanent" it is meant that such a connection may be made for a matter of several minutes up to several days, as may be required and determined by an attending physician or other medical personnel.

It is also evident, from FIG. 4, that depression of the valve element 36 by advancing the end 70 of a male luer taper 54 against the upper face 60, 62 of the valve structure, will open the valve, whether or not a luer lock is employed.

Any other suitable configuration may also be provided at the outer surface of the injection end, such as a double thread, to conform the outer surface to be received in and mate to a standard ISO or ANSI luer lock collar.

In general, the intravenous injection site 30 of the present invention is conformed having the interior diameter of the first passageway 46 to be slightly larger than the outer diameter of a standard ISO or ANSI male luer taper 54.

In a preferred embodiment of the one-piece combination element 33 according to the present invention, the valve portion 36 is configured so as to have a centrally located cylindrical neck portion 80 which extends in a direction away from the valve seating face 64 up to the upper face 62. The upper face 62 has a channel 82 formed in it; and for ease of establishing fluid communication from the first passageway 46 and past the annular valve seat 40, and the valve seating face 64 to the second passageway 48, the channel 82 is formed in a direction which is perpendicular to a line drawn between the pair of diametrically opposed strap portions 38.

Moreover, while not necessary, it is usual that the channel 82 is formed having a bottom surface that has a centrally located apex 84, and a pair of sloping bottom surface elements 86, 88, that are sloped away from the apex 84 and in a direction away from the upper surface 62. This structure may assure better fluid flow, especially for viscous fluids such as certain medications, nutrient solutions, or blood, as they may flow from or to the interior 88 of the male luer taper 54, through the channel 82 and past the valve annular valve seat 40 and the valve seating face 64.

Thus, when a standard ISO or ANSI male luer taper 54 is passed into the first passageway 46 so as to contact the upper face 62 of the valve portion 36, fluid communication from the interior 88 of the male luer taper 54 is established, as discussed above.

Referring particularly to FIGS. 5, 6, and 7, it can be seen that a standard ISO or ANSI male luer taper 54 may best be accommodated in the first passageway 46 by recessing each of the strap portions 38 into a co-operating recess 90 formed in the interior walls of the first passageway 46. This permits the male luer taper 54 to pass unimpeded into the passageway 46.

So as to better assure the wipeability of the outer surface of the septum portion 34, that surface may be formed so as to present a slightly convex wipeable septum surface at the exterior of the injection end 42, as can be seen in each of FIGS. 6 and 8.

Likewise, the lower surface 66 of the valve portion 36 may be formed so as to be a slightly convex surface. This may also assist in the requirement for the valve structure including valve element 36 and opposed annular valve seat 40 and valve seating face 64 to withstand considerable back pressure to which it may, from time to time, be subjected. For example, a circumstance may develop where an anaesthetist has an anaesthetic injection syringe or other structure connected at the upper "Y"-site in the intravenous set shown in FIG. 1, and he might suddenly be required to inject anaesthetic through the injection site at such as pressure that pressures as much as 40 psi or 45 psi might build against the underside of the valve structure at the lower "Y"-site, as shown in the intravenous set of FIG. 1. Indeed, the ability to withstand such back pressure in the range of 40 psi to 45 psi is becoming more of a requirement in the acceptance standards for intravenous injection sites as they are being laid down by hospital purchasing agents acting on the direction of the hospital administrator.

As particularly noted in FIG. 8, the upper end of the first passageway 46 may be formed with a pair of undercuts 92 formed therein. Thus, as can be seen in FIG. 4, when the blunt cannula or male luer taper is passed through the slit 50 of the septum portion 34, the portions of the septum 34 on either side of the slit 50 may fold into the undercuts 92. Once again, this assures easy passage and accommodation of the blunt cannula or male luer taper 54 into the upper or first passageway 46.

Moreover, as is seen particularly in FIGS. 3, 4, 6, and 8, the upper portion of the combination element may be formed so as to have a sleeve portion 94 which extends around and downwardly from the outer surface of the septum portion 34. This permits the sleeve portion 94 to be placed over the outer surface of the substantially rigid housing 30 at the injection end 42 thereof. The sleeve portion 94 is typically accommodated in a further exterior undercut 96.

Still further, an appropriate pair of openings 75 may be formed in the sleeve portion 94 so as to accommodate the pair of lugs 74, as shown in FIGS. 4 and 6. Thus, even when the septum portion is formed so as to present the sleeve portion 94 which is placed over the outer surface of the substantially rigid housing 32 at the injection end 42 thereof and over the lugs 74, it will still be accommodated in a standard ISO or ANSI luer lock collar such as the collar 58 shown in FIG. 4.

Returning to FIG. 1, it has been shown that a medical intravenous injection site in keeping with the present invention may have the configuration of a "Y"-site. There, a further passageway may be formed such as the passageway shown at 47. That passageway also has a second input end which faces in the same general direction as the injection end of the passageway 46a, as shown, so that each of the passageways are in fluid communication with the exit passageway 48a, as shown. Thus, the patient end of either "Y"-site 18 is located at the end of the respective substantially rigid housing for that "Y"-site at the end of the exit passageway which is remote from both the injection end and the second input end.

In general, the annular valve seat 40 and the valve seating face 64 are formed so that each is sloped downwardly and outwardly with respect to the first passageway 46. This configuration also may contribute to improved fluid flow, particularly of viscous fluids, as well as contributing to the ability of the valve element 36 together with the annular valve seat 40 and valve seating face 64 to withstand back pressure.

Various materials may be employed for manufacture of the one-piece elastomeric septum and valve combination element. The choice of such materials may be determined by a number of factors, including its tear strength and its stretchability or elasticity. Whatever material is employed, is should be easily moldable; and it is desirable that the material should be such that no post curing is required, after the element has been removed from the mold. In general, the slit 50 is molded into the septum portion of the combination element 33 while it is being molded, although the slit may be placed or cut into the septum portion after it has been molded.

Another consideration as to the material to be used includes its wipeability, and whether it will exhibit any indication of deterioration after it may have been wiped as many as forty or sixty, or up to one hundred, times. As stated above, the usual wiping solution is 70% isopropyl alcohol.

It is generally desirable that the material of the septum, and thus the material of the combination element 33, shall be free of latex, although that consideration is not specifically important. Other considerations include the ability of the material to be bonded using appropriate adhesives, so that it may be put into place over the injection end of the housing of a medical intravenous injection site in keeping with the present invention.

Some typical materials which can be employed for the production of the combination element 33 include various medical grades of silicone rubber such as those which may be available from Applied Silicone Corporation, or NuSil Technology Corporation. Such silicone rubbers will normally have a durometer hardness in the range of 20 to 70, measured on the Shore A durometer hardness scale.

Other appropriate materials are SEBS thermoplastic elastomers, which are styrene-ethylene/butylene-styrene block terpolymers, and which are available from Consolidated Polymer Technologies Inc. Those materials may have durometer Shore A hardness in the range of 20 to 50.

The material from which the housing 32 is injection molded is typically polyvinylchloride, although other medical grade thermoplastic materials may also be employed.

There has been described a medical intravenous injection site which comprises a single one-piece elastomeric septum and valve combination element which is placed in and over a substantially rigid housing so as to present a wipeable septum and a two-way valve structure which may be opened by using a blunt cannula. Specifically, the blunt cannula which is particularly intended to be used with the medical intravenous injection site of the present invention may be a standard ISO or ANSI male luer taper. Prospectively, a single strap portion which is formed as pan of the combination septum and valve combination element may be used, but usually a pair of opposed strap portions are provided.

The injection end of the medical intravenous injection site may be configured and dimensioned so as to meet all appropriate ISO or ANSI luer lock standards. Moreover, the valve construction in keeping with the present invention may be opened without the necessity of establishing a luer lock arrangement.

Of course, medical intravenous injection sites in keeping with the present invention may be configured as a single access injection site, or as a "Y"-site. If the medical intravenous injection site is configured as a "Y"-site, one or both of the injection input passageways of the "Y"-site may be provided with a valve structure in keeping with the present invention, although usually only input arm of a "Y"-site is so provided. This latter arrangement permits the intravenous injection site to be employed in an intravenous set together with appropriate catheters, drip bags, medication injectors, and the like, whereby the injection site may be used from time to time either to inject other medications, nutrients, anesthetics, or the like, or to withdraw blood or other body fluids from the patient. In order for that to occur, however, the medical intravenous injection site of the present invention has been provided with a wipeable septum.

Still further, injection sites in keeping with the present invention may be found to be particularly useful in other catheter sets or catheter sampling or disposal systems, such as with urinary catheters or bile bag sets. The valve permits the site to remain in its closed condition except when a biological body fluid sample is required, which sample may then be withdrawn through the site using a male luer taper or other appropriate blunt cannula so as to cause the valve structure to temporarily open.

Other embodiments of or amendments to the construction of a medical intravenous injection site, apart from those which have been described above, may be adopted without, however, departing from the spirit and scope of the appended claims.

What is claimed is:

1. A medical intravenous injection site comprising a rigid housing having, an elastomeric septum and an elastomeric valve element mounted therein, said medical intravenous injection site being adapted to receive a blunt cannula inserted through said septum;

wherein said rigid housing has a first, injection end and a second, patient end, and is configured so as to have an internally disposed annular valve seat formed therein; said rigid housing having a first opening at said injection end thereof, a second opening at said patient end thereof, a first passageway extending between said first opening and said annular valve seat, and a second passageway extending between said annular valve seat and said second end, said first and second passageways connecting said first and second ends of said rigid housing in fluid communication one with the other;

wherein said elastomeric septum and said elastomeric valve element comprise a single, one-piece elastomeric septum and valve combination element having a septum portion, a valve portion, and at least one strap portion extending therebetween;

wherein said septum portion is positioned at said injection end of said rigid housing so as to cover said first opening, and so as to present a wipeable septum surface at the exterior of said injection end;

wherein said patient end of said rigid housing is configured as a socket so as to connect to an end of an intravenous tube;

wherein said septum portion has at least one elongate slit formed therein through its thickness, and said elastomeric septum portion is deformable so as to permit a blunt cannula to pass through said slit and into said first passageway;

wherein said valve portion has an upper face which faces towards said septum portion, a valve seating face which co-operates with said annular valve seat so as to form a closeable valve when said valve seating face and said annular valve seat are in contact with each other, and a lower surface opposed to said upper face and said valve seating face;

wherein the length of said at least one elastomeric strap portion is such as to urge said valve seating face into contact with said annular valve seat when said strap portion is at rest and is not distended beyond its rest position; and wherein said at least one strap portion is distendable so that said valve portion may be moved away from said annular valve seat towards said second end when a blunt cannula contacts said upper face of said valve portion and is advanced thereagainst so as to distend said at least one strap portion, whereby said closeable valve is opened so as to permit fluid flow therepast in either direction between said first passageway and said second passageway.

2. The medical intravenous injection site of claim 1, wherein said single, one-piece elastomeric septum and valve combination element has a pair of diametrically opposed strap portions extending between said septum portion and said valve portion.

3. The medical intravenous injection site of claim 2, wherein said first passageway has a pair of co-operating recesses in the interior walls thereof, and wherein each of said pair of diametrically opposed strap portions is recessed into a respective co-operating recess.

4. The medical intravenous injection site of claim 3, wherein said valve portion is configured so as to have a centrally located cylindrical neck portion extending away from said valve seating face up to said upper face, and said upper face has a channel formed therein in a direction perpendicular to a line drawn between said pair of diametrically opposed strap portions, so as to provide a fluid flow pathway.

5. The medical intravenous injection site of claim 4, wherein said channel has a bottom surface having a centrally located apex and a pair of sloping bottom surface elements sloped away from said apex in a direction away from said upper surface.

6. The medical intravenous injection site of claim 5, wherein the interior diameter of said first passageway is slightly larger than the outer diameter of a standard ISO or ANSI male luer slip or male luer taper, so that when a standard ISO or ANSI male luer slip or male luer taper is passed into said first passageway so as to contact said upper face of said valve portion, and said closeable valve is opened, fluid communication is established from the interior of said male luer slip or male luer taper, through said channel, past said cylindrical neck portion, between said annular valve seat and said valve seating face, and into said second passageway;

whereby fluids may flow from said injection end to said patient end of said housing, or vice versa.

7. The medical intravenous injection site of claim 2, wherein said septum portion has a single slit formed therein, and is adapted to receive a standard ISO or ANSI male luer slip or male luer taper as a blunt cannula to be passed through said single slit into said first passageway, so as to contact said upper face of said valve portion, and so as to cause said pair of diametrically opposed strap portions to distend and to open said closeable valve.

8. The medical intravenous injection site of claim 7, wherein said rigid housing has an outer surface at said injection end, and is conformed on said outer surface so as to be received in and mate to a standard ISO or ANSI luer lock collar associated with said male luer slip or male luer taper.

9. The medical intravenous injection site of claim 8, wherein said outer surface of said injection end of said rigid housing has a pair of diametrically opposed lugs to be received in a standard ISO or ANSI luer lock collar.

10. The medical intravenous injection site of claim 8, wherein said septum portion is formed so as to present a sleeve portion thereof which is placed over said outer surface of said rigid housing at the injection end thereof;

and wherein said outer surface of said rigid housing is formed at said injection end thereof so as to accommodate said sleeve portion, whereby said injection end may be accommodated in a standard ISO or ANSI luer lock collar.

11. The medical intravenous injection site of claim 8, wherein said rigid housing is formed as a Y-site, having said first and second passageways in fluid communication to an exit passageway formed therein;

wherein a further passageway is formed having a second input end facing in the same general direction as said injection end, and said further passageway is in fluid communication with said exit passageway; and wherein said patient end of said rigid housing is located at the end of said exit passageway remote from said injection end and said second input end.

12. The medical intravenous injection site of claim 1, wherein said septum portion is formed so as to present a slightly convex wipeable septum surface at said exterior of said injection end.

13. The medical intravenous injection site of claim 1, wherein said lower surface of said valve portion is formed so as to be a slightly convex surface.

14. The medical intravenous injection site of claim 1, wherein said first passageway is formed at an upper end thereof coincident with said first opening of said rigid housing so as to have an undercut formed in the interior walls of said first passageway so as to accommodate said septum portion, whereby said septum portion may be folded into said undercut when a blunt cannula is passed through said slit.

15. The medical intravenous injection site of claim 1, wherein said septum portion is formed so as to present a sleeve portion thereof which is placed over the outer surface of said rigid housing at the injection end thereof.

16. The medical intravenous injection site of claim 1, wherein said at least one elongate slit is formed so as to extend substantially completely across a diameter of said septum portion.

17. The medical intravenous injection site of claim 1, wherein each of said annular valve seat and said valve seating face are formed so as to be sloped downwardly and outwardly with respect to said first passageway.

18. The medical intravenous injection site of claim 1, wherein said single, one-piece elastomeric septum and valve combination element is formed from a moldable material having a durometer hardness in the range of 20 to 70 on the Shore A scale.

19. The medical intravenous injection site of claim 18, where the moldable material is chosen from the group consisting of silicone rubber having a Shore A durometer hardness in the range of 30 to 70, and styrene-ethylene/butylene-styrene block terpolymers having a Shore A durometer hardness in the range of 20 to 50.

* * * * *